United States Patent [19]

Crainich

[11] Patent Number: 5,658,297
[45] Date of Patent: Aug. 19, 1997

[54] SURGICAL STAPLE REMOVER

[76] Inventor: Lawrence Crainich, Ceda Rd., Charlestown, N.H. 03603

[21] Appl. No.: 405,303

[22] Filed: Mar. 16, 1995

[51] Int. Cl.$^6$ ............................................. A61B 17/10
[52] U.S. Cl. ............................................. 606/138
[58] Field of Search ........................... 606/138, 206, 606/208; 254/28; 132/330; 227/63

[56] References Cited

U.S. PATENT DOCUMENTS

| | | | |
|---|---|---|---|
| 2,202,984 | 6/1940 | Drypolcher | 254/28 |
| 2,887,110 | 5/1959 | Roeschmann | 128/321 |
| 3,254,649 | 6/1966 | Wood | 128/321 |
| 3,283,557 | 11/1966 | Wood | 72/386 |
| 3,344,649 | 10/1967 | Wood | 72/392 |
| 3,817,078 | 6/1974 | Reed et al. | 72/392 |
| 4,026,520 | 5/1977 | Rothfuss et al. | 254/28 |
| 4,462,404 | 7/1984 | Schwarz et al. | 606/206 |

*Primary Examiner*—Guy V. Tucker
*Assistant Examiner*—Tina T. D. Pham
*Attorney, Agent, or Firm*—Bachman & LaPointe, P.C.

[57] ABSTRACT

A surgical staple remover includes a first elongate member having a forward first end, a rearward second end and a central portion therebetween, the first end terminating in two spaced anvil members, a second elongate member having a forward first end, a rearward second end and a central portion therebetween, the first end terminating in a blade member adapted to fit between the two spaced anvil members, a releasable pivot member for releasably and pivotably joining the first end of the first member and the first end of the second member at a pivot point, and a releasable joining member for joining the second end of the first member and the second end of the second member and for holding the releasable pivot member in a pivotably joined position, at least one of the first and second members being at least partially bowed whereby movement of the central portion of the first member relative to the central portion of the second member provides pivot of the anvil members relative to the blade member.

19 Claims, 2 Drawing Sheets

5,658,297

1

SURGICAL STAPLE REMOVER

BACKGROUND OF THE INVENTION

The invention relates to a medical instrument and, specifically, to an improved surgical staple remover.

Numerous devices have been disclosed for use in removing surgical staples after a healing process has been sufficiently completed. The surgical staples to be removed typically have a bale portion with two side arm portions depending therefrom and two inwardly directed sharpened tips which generally have been driven into the skin or tissue to be joined by the staple. Thus, in a closed position, the staple has a substantially rectangular or closed shape.

Surgical staple removers are known which remove such staples by positioning spaced anvils beneath the bale portion and a blade member above the bale portion. Downward relative movement of the blade portion serves to bend the bale portion of the staple into a generally U-shape causing the arms to deflect outwardly and away from the tissue of the patient. U.S. Pat. No. 4,026,520 to Rothfuss et al. is an example of a known surgical staple extractor which operates as described above.

Although numerous disclosures regarding staple extractors have been made, the need still exists for a surgical staple extractor which is simple in structure and manufacture and reliable in use.

It is therefore the principal object of the present invention to provide a surgical staple remover which is simple in design and, therefore, less expensive to manufacture.

It is a further object of the present invention to provide such a surgical staple remover which can be sterilized in a conventional autoclave for re-use as desired.

It is another object of the present invention to provide a surgical staple remover which is simple and reliable in use.

It is still another object of the present invention to provide a surgical staple remover having stop means for preventing over-opening of a staple being removed.

Other objects and advantages of the present invention will appear hereinbelow.

SUMMARY OF THE INVENTION

In accordance with the present invention, the foregoing objects and advantages are readily attained.

According to the invention, a surgical staple remover is provided comprising a first elongate member having a forward first end, a rearward second end and a central portion therebetween, said first end terminating in two spaced anvil members, a second elongate member having a forward first end, a rearward second end and a central portion therebetween, said first end terminating in a blade member adapted to fit between said two spaced anvil members, releasable pivot means for releasably and pivotably joining said first end of said first member and said first end of said second member at a pivot point, and releasable joining means for joining said second end of said first member and said second end of said second member and for holding said releasable pivot means in a pivotably joined position, at least one of said first and second members being at least partially bowed whereby movement of said central portion of said first member relative to said central portion of said second member provides pivot of said anvil members relative to said blade member.

In accordance with the foregoing, a surgical staple remover is provided which is extraordinarily simple in manufacture, which is readily separable into two integral parts which are easily sterilized in a conventional autoclave, and which is simple and reliable in use.

BRIEF DESCRIPTION OF THE DRAWINGS

A detailed description of the preferred embodiments of the invention follows, with reference to the attached drawings wherein.

DETAILED DESCRIPTION

The invention relates to a surgical staple remover for removing surgical staples which are widely used in the medical field for closing wounds, incisions and the like in the skin or tissue of a patient.

Figure 1:
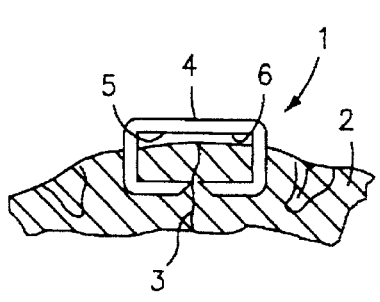
FIG. 1 illustrates a surgical staple in a closed position.
Figure 2:
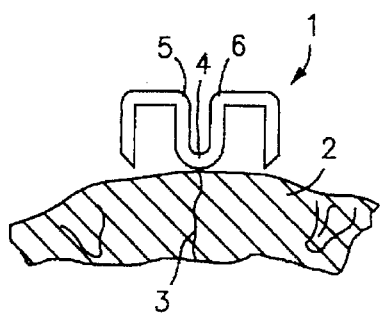
FIG. 2 illustrates a surgical staple in an open position after it has been acted upon by the staple remover according to the present invention.

FIG. 1 illustrates a surgical staple 1 in place in the skin or tissue 2 of a patient for closing a wound 3 therein. When the wound has healed sufficiently, surgical staple 1 must be removed. According to the invention, a staple remover is provided for removing the staple through application of a downward force in the vicinity of point 4 and upward forces in the vicinity of points 5 and 6 so as to deform the bale portion or upper portion of the staple and pivot the arms and sharpened points of the staple out of and away from the tissue of the patient. FIG. 2 illustrates the open position of such a staple after opening by a surgical staple remover such as that of the present invention. According to the invention, a staple remover is provided which is simple both in manufacture and in use for opening and removing staples.

Figure 3:
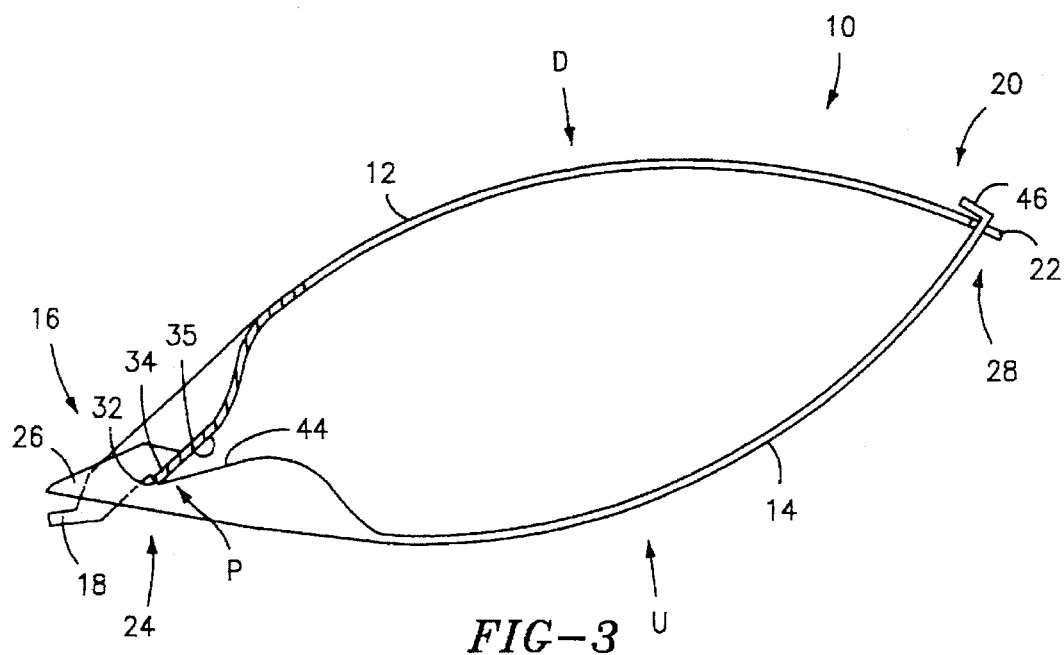
FIG. 3 is a partially sectional side view of a surgical staple remover in accordance with the invention.

FIG. 3 illustrates a surgical staple remover 10 according to the invention. Remover 10 has a first member 12 and a second member 14, each of which is preferably elongate and bowed along a central portion or length thereof, and preferably made from a resilient material as will be discussed below. According to the invention, first member 12 has a forward end 16 which terminates in two spaced anvil members 18, and a rearward end 20 preferably having a tab portion 22 extending therefrom which will be discussed further below.

Figures 6, 7:
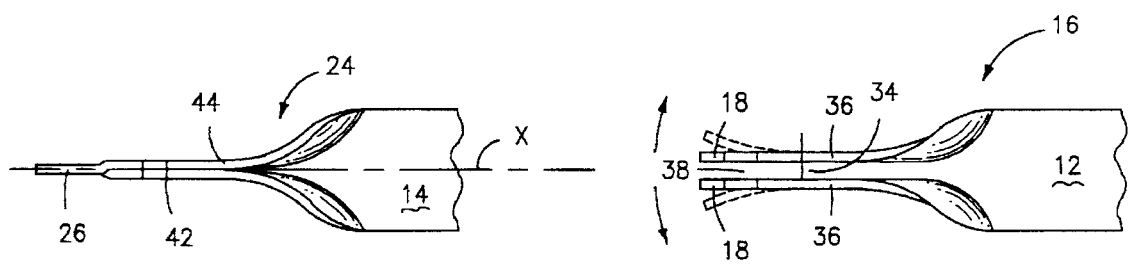
FIG. 6 is a top view of the forward portion of the anvil element of the surgical staple remover according to the invention.
FIG. 7 is a top view of the forward portion of the blade element of the surgical staple remover according to the invention.
Figure 8:
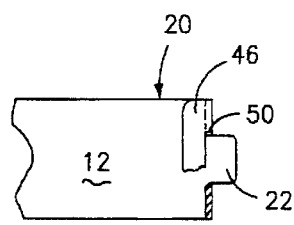
FIG. 8 is a partially sectional view of the rearward portion of a surgical staple remover according to the invention.

Referring to FIG. 6, forward end 16 of first member 12 is further illustrated. As shown, anvil members 18 are preferably defined at the end of two spaced, generally parallel upstanding walls 36 arranged at forward end 16. Anvil members 18 may be formed to provide any suitable and desirable shape, and preferably extend generally laterally as shown. In use, anvil members 18 serve to apply the desired force in the vicinity of points 5 and 6 of a staple to be removed. A transverse portion or rib 34 is preferably provided between walls 36 as shown.

Second member 14 has a forward end 24 terminating in a blade member 26 adapted to fit between anvil members 18 of first member 12, and a rearward end 28 preferably having a fold 48 and an aperture 50 for receiving rearward end 20 and tab 22 of first member 12 as will be discussed below. One anvil member 18 of first member 12 is sectioned away in FIG. 3 so as to illustrate blade member 26 of second member 14 in greater detail. Blade member 26 may also be provided of any desirable shape and is also preferably provided as a generally laterally extending member as shown. In use, blade member 26 serves to apply the desired force to a staple being removed in the vicinity of point 4.

Referring to FIG. 7, forward end 24 of second member 14 is further illustrated. As shown, blade member 26 is preferably formed from upwardly deformed side portions of forward end 24 so as to define a single upstanding blade member 26. A notch 32 (FIG. 3) is preferably provided in second member 14 at forward end 24 and positioned rearward of blade 26. Notch 32 preferably opens facing generally rearwardly, toward rearward end 20 as shown.

According to the invention, first member 12 and second member 14 are releasably and pivotably connected or linked at a pivot point P which is preferably positioned just rearwardly of blade member 26 and anvil members 18. Pivot point P is releasably established through cooperation between notch 32 and transverse rib member 34. Notch 32 serves to receive rib 34 in a pivotable manner such that blade 26 and anvils 18 are pivotable relative to each other around pivot point P.

In further accordance with the invention, tab 22 of end 20 and fold 48 with aperture 50 of end 28 serve to provide a joining structure for joining rearward ends 20, 28 and for holding notch 32 and rib 34 in a pivotably connected position. Tab 22 is preferably sized to be received in aperture 50. End 20 is received in fold 48 with tab 22 inserted into aperture 50 so as to provide secure but releasable joining of ends 20, 28 in accordance with the invention.

Figure 4:
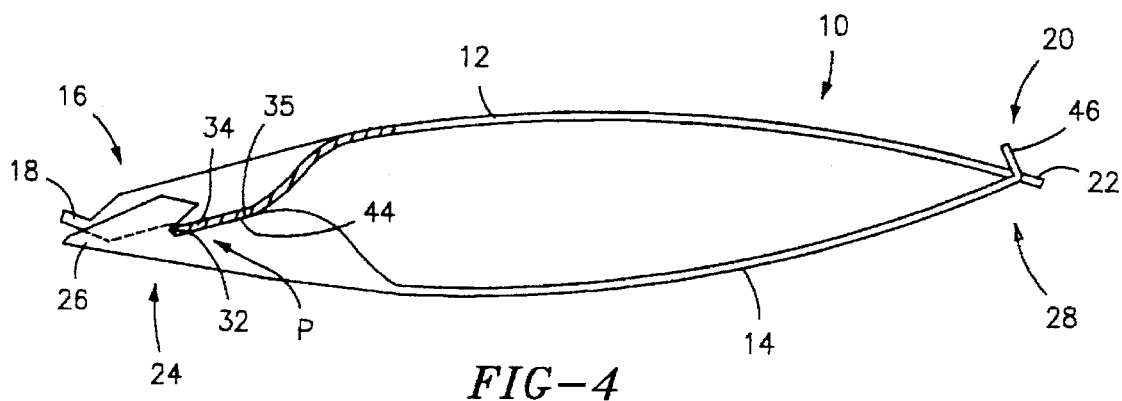
FIG. 4 is a partially sectional side view of the surgical staple remover of FIG. 3 in a compressed position.

First and second members 12, 14 are preferably made from a resilient, deformable material such as spring metal or the like, preferably so that members 12, 14 can be bent, deformed or flexed during use and will return to substantially the same starting position. In accordance with the invention, staple remover 10 is operated by compressing members 12, 14 toward one another to the position illustrated in FIG. 4. This compression causes relative pivot of anvil members 18 and blade member 26 toward each other. Anvil members 18 apply the upward force at points 5, 6 as shown in FIG. 1 while blade member 26 applies a downward force at point 4, also shown in FIG. 1, so as to open the staple as desired.

As set forth above, members 12, 14 are preferably provided from a resilient material whereby, upon release of the compressive force directed toward members 12, 14, staple remover 10 returns to its original position as illustrated in FIG. 3 for use in the next staple removal operation.

According to the invention, staple remover 10 is both extraordinarily simple in manufacture and readily separable into two integral elements, each ideally suited for sterilization in an autoclave and the like for re-use as desired. Further, staple remover 10 is desirably simple and reliable in use.

Figure 5:
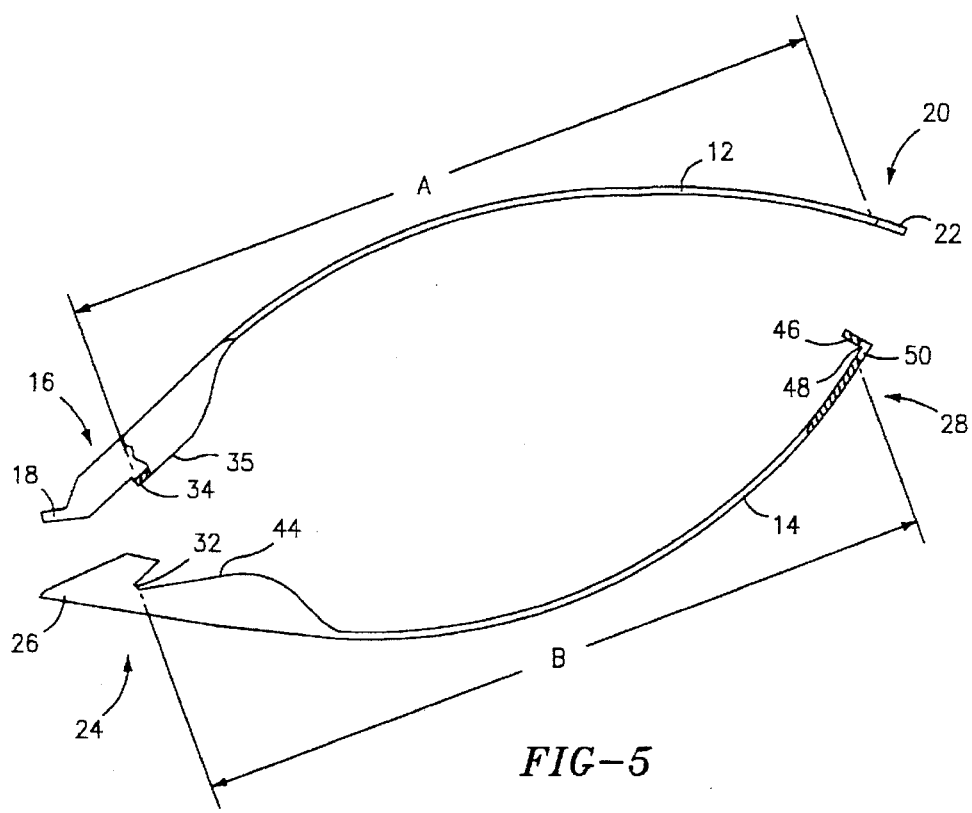
FIG. 5 is an exploded view of the surgical staple remover of FIG. 3 in a dis-assembled position.

FIG. 5 is an exploded view of staple remover 10 further illustrating the features of members 12, 14. According to the invention, members 12, 14 are preferably formed from substantially flat strips of resilient metal which may be formed or otherwise machined in accordance with conventional techniques so as to provide the desired structure in a simple and cost-effective manner.

Members 12, 14 are preferably bowed at least along a central portion thereof between forward and rearward ends 16, 24 and 20, 28, respectively. The bowed portion is bowed along the length of members 12, 14, as shown in the drawings, so that the bowed portion is bowed around a transverse axis with respect to the length of member 12, 14. Members 12, 14 preferably also have a substantially flat transverse cross-section as shown.

Member 12 is preferably bowed so as to have a generally downwardly facing concave side or portion defined by the bowed portion when member 12 is in a generally upright position as shown.

Second member 14 is also preferably bowed so as to define a generally upwardly facing concave side or portion. According to the invention, the concave sides of first and second members 12, 14 are preferably arranged so as to face each other when staple remover 10 is assembled. Thus, compression or relative movement of central portions of members 12, 14, for example the application of downward force D and upward force U on members 12, 14, respectively, as shown in FIG. 3, serves to bias members 12, 14 against the bowed normal position thereof into the compressed position illustrated in FIG. 4, and provides pivot of anvil members 18 relative to blade member 26 as desired. Compression of members 12, 14 to the position of FIG. 4 pivots blade member 26 relative to anvil members 18 so that blade member 26 at least partially passes between anvil members 18 to apply forces to a staple being opened as discussed above. Upon release or removal of forces D, U, staple remover 10 returns to its uncompressed position for use in the next removal procedure.

In accordance with the invention, when staple remover 10 is assembled, it is preferable that member 12 be slightly in compression and member 14 be slightly in tension. This serves to firmly hold members 12, 14 together while allowing their separation as desired and as will be discussed below. Referring to FIG. 5, member 12 may preferably be provided having a length A from rib 34 to rearward end 20, while member 14 is preferably provided having a length B from notch 32 to fold 48. In accordance with the invention, length A is preferably greater than length B when members 12, 14 are separated or dis-assembled. This configuration of members 12, 14 serves to place member 12 in compression and member 14 in tension when staple remover 10 is assembled. The desired states of compression and tension are provided by the compressive force exerted upon member 12 by member 14 and the tensile force exerted upon member 14 by member 12 due to the accommodation of length A within length B.

As best shown in FIG. 6, the side portions of member 12 at forward end 16 are preferably bent or otherwise formed upwardly in accordance with the invention so as to define two generally upstanding wall members 36 each terminating in an anvil member 18. According to the invention, wall members 36 are preferably spaced sufficiently to define a gap 38 therebetween for receiving blade member 26 as will be further described below. As best illustrated in FIG. 6, the longitudinal central portion of the forward end 16 of first member 12 is preferably cut away or removed so as to further define gap 38. Transverse rib 34 is positioned at a rearward end of the cut away central portion of gap 38, and joins the lower portions of walls 36.

In use, anvil members 18 on walls 36 are flexible and can be laterally deflected away from each other as shown, for example, in FIG. 6. This flexibility and lateral deflectability of anvil members 18 is desirable so as to accommodate use of staple remover 10 in removing staples having bale portions 4 of varying widths. During removal of a staple, anvil members 18 tended to laterally deflect until seated in the corner between the bale portions and arm portions of the staple. This seating of anvil members 18 in a staple being removed serves advantageously to provide enhanced reliability of the removal operation.

In accordance with the invention, forward end 24 of second member 14 is preferably bent generally upwardly along a longitudinal central axis X (see FIG. 7) thereof so as to define a single upstanding wall 42 terminating in blade member 26. According to the invention, blade member 26 is sized so as to pass within or through gap 38 defined between walls 36 of first member 12. According to the invention, upstanding wall 42 of second member 14 is preferably provided with notch 32 opening generally rearwardly as shown. Notch 32 serves to pivotably receive the leading edge of transverse rib 34. Upstanding wall 42 further preferably has an upstanding raised rib or stop portion 44 arranged for contact with an abutment surface 35 arranged rearwardly of transverse rib 34 of first member 12 so as to define a maximum closed or compressed position for staple remover 10. According to the invention, stop member 44 extends upwardly a predetermined distance so that stop member 44 contacts rib 34 at a predetermined maximum closing position, thereby stopping pivot of blade member 26 relative to anvil members 18 at a desired compressed position and preventing over-opening of a staple to be removed. This is desirable as the additional deformation of staple 1 beyond the state illustrated in FIG. 2 which may result from over-opening may rupture the staple into two elements and/or dislodge the staple being removed from the firm grasp of anvil members 18 and blade member 26 causing undesirable complications.

According to the invention, the rearward opening orientation of notch 32 of second member 14 provides for separation of first member 12 from second member 14 as desired by rearwardly deflecting or displacing first member 12 relative to second member 14. Such rearward displacement of first member 12 serves to remove transverse rib 34 from notch 32 thereby releasing the pivotable connection at pivot point P.

According to the invention, first member 12 and second member 14 are held against separation in a linked or assembled position by tab 22 of end 20 and fold 48 with aperture 50 of end 28 which define a joining structure for joining ends 20, 28 and for releasably holding first member 12 against rearward deflection relative to second member 14. As illustrated in FIG. 5, first member 12 preferably has tab member 22 projecting from end 20 thereof, while second member 14 preferably has an upstanding ledge or angled member 46 which is bent relative to end 28 of second member 14 so as to define fold 48 therebetween. Further, as set forth above, aperture 50 is preferably provided in second end 28 of second member 14, preferably substantially aligned with fold 48. Aperture 50 preferably extends to both sides of fold 48, into member 46 and end 28 of second member 14, with fold 48 passing through aperture 50. Fold 48 serves to receive the edge of rearward end 20 of first member 12, while aperture 50 receives tab 22 so as to releasably hold first member 12 between notch 32 and fold 48/aperture 50 structure of second member 14. Fold 48 and ends 20 preferably have generally lateral orientation. This is desirable because, in accordance with the invention, the interaction of end 20 with fold 48 thereby serves to provide the assembled staple remover 10 with additional stability.

According to the invention, and as set forth above, first and second members 12, 14 are readily releasable from the joined or linked position illustrated in FIG. 3. This releasability is desirable and advantageous in accordance with the invention as members 12, 14 when separated are more readily sterilized in accordance with conventional techniques, for example in an autoclave. Separation of members 12, 14 is effected by first disengaging ends 20, 28 by disengaging tab 22 and end 20 from aperture 50 and fold 48 when rearward ends 20, 28 are disengaged. First member 12 may then be rearwardly displaced relative to second member 14 so as to remove transverse or lateral rib 34 from notch 32 and to thereby disengage ends 16, 24 as well, thereby effecting separation of members 12, 14 as desired.

Of course, the procedure is readily reversible so as to reassemble members 12, 14, for example after sterilization. First, rib 34 is pushed or disposed into notch 32, then tab 22 and end 20 are engaged with fold 48 and aperture 50 of end 28 so as to join ends 20, 28, thus providing assembled staple remover 10 ready for use in accordance with the invention.

It should be noted that the staple remover 10 in accordance with the present invention is provided from a minimum number of parts which are readily disassembled for effective sterilization. Staple remover 10 in accordance with the present invention is simplified for efficient manufacture and is more readily sterilizable than conventional staple removal devices. Further, staple remover 10 according to the invention is simple and reliable in use.

It should of course be noted that while this disclosure is made in terms of notch 32 being positioned on second member 14 and transverse rib 34 being positioned on first member 12, rib 34 and notch 32 could of course be reversed in their positioning on members 12, 14, as could tab 22, fold 48 and aperture 50, all within the scope of the present invention.

It should also be noted that while the members 12, 14 are disclosed as being preferably made of a resilient spring metal, other materials could of course be used. While members 12, 14 are disclosed in terms of being substantially bowed or having a bow-shape, such members need not be bowed along their entire length. A single bend could for example be provided at some point along the length of members 12, 14 rather than the gradual arc as described in accordance with the preferred embodiment disclosed herein. Further, a portion less than the entire length of member 12, 14 could be bowed. In addition, while it is preferred that both members 12, 14 be bowed, a bowed portion could be provided in just one of members 12, 14 if desired.

Thus disclosed is a surgical staple remover in accordance with the present invention which is extraordinarily simple in manufacture, thereby advantageously providing a device which is also readily sterilizable due to its simple structure. Additional springs, axles and other complicating features of prior art devices are avoided by the surgical staple remover according to the present invention, thereby further simplifying the elements of the device for both manufacture and sterilization, and providing a staple remover which is therefore simple and reliable in use.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

I claim:

1. A surgical staple remover, comprising:
   a first elongate member having a forward first end, a rearward second end and a central portion therebetween, said first end terminating in two spaced anvil members;
   a second elongate member having a forward first end, a rearward second end and a central portion therebetween, said first end terminating in a blade member adapted to fit between said two spaced anvil members;
   releasable pivot means for releasably and pivotably joining said first end of said first member and said first end of said second member at a pivot point; and
   releasable joining means for joining said second end of said first member and said second end of said second member and for holding said releasable pivot means in a pivotably joined position, at least one of said first and second members being at least partially bowed whereby movement of said central portion of said first member relative to said central portion of said second member provides pivot of said anvil members relative to said blade member.

2. A surgical staple remover according to claim 1, wherein said releasable pivot means comprises a transverse element positioned on said first member and a notch positioned on said second member for receiving said transverse element, and wherein said releasable joining means is adapted to releasably hold said transverse element within said notch.

3. A surgical staple remover according to claim 1, wherein said first and second members are biased toward an open position wherein said blade member is positioned above said two spaced anvil members, and wherein said central portion of said first member and central portion of said second member are compressible toward each other to a compressed position wherein at least one of said blade member and said two spaced anvil members is pivoted toward the other whereby said blade member at least partially passes between said two spaced anvil members.

4. A surgical staple remover according to claim 3, further comprising stop means positioned on one of said first and second members for stopping pivot of said blade member and said two spaced anvil members at a preselected compressed position, whereby over-opening of a staple to be removed is avoided.

5. A surgical staple remover according to claim 4, wherein said stop means comprises a raised rib positioned on said second member rearwardly of said blade member and an abutment surface positioned on said first member rearwardly of said anvil member for contact with said raised rib at said preselected compressed position, whereby further pivot of said blade member and said two spaced anvil members is stopped at said preselected compressed position.

6. A surgical staple remover according to claim 1, wherein said releasable joining means comprises an aperture on said second end of one of said first and second members, and a tab member on said second end of the other of said first and second members, said tab member being sized to be received in said aperture.

7. A surgical staple remover according to claim 6, wherein said second end at which said aperture is positioned has a ledge member arranged at an angle to said second end and defining a substantially transverse fold therebetween for receiving said second end of said other of said first and second members, said fold passing through said aperture.

8. A surgical staple remover according to claim 1, wherein said first and second members each comprise an elongate member having a substantially flat transverse cross-section.

9. A surgical staple remover according to claim 8, wherein said first end of said first member has two spaced upstanding walls, each wall terminating in one of said two spaced anvil members, and wherein said first end of said second member has a single upstanding wall terminating in said blade member.

10. A surgical staple remover according to claim 9, wherein said releasable pivot means comprises a notch defined on said single upstanding wall rearwardly of said blade member and a transverse portion joining lower ends of said two spaced upstanding walls and arranged rearwardly of said two spaced anvil members, said notch being adapted to pivotably receive said transverse portion whereby said first end of said first member and said first end of said second member are releasably pivotably joined at a pivot point.

11. A surgical staple remover according to claim 1, wherein said first member and said second member have an assembled position wherein said first end of said first member and said first end of said second member are pivotably joined and said second end of said first member and said second end of said second member are releasably joined, and a dis-assembled position wherein at least one of said first ends of said first and second members and said second ends of said first and second members are separated, wherein said first member has a first length and said second member has a second length, and wherein, in said disassembled position, one of said first and second lengths is longer than the other of said first and second lengths, whereby, in said assembled position, one of said first and second members is in tension and the other of said first and second members is in compression.

12. A surgical staple remover according to claim 1, wherein at least one of said first member and said second member has a bowed portion positioned between said first end and said second end, and wherein said bowed portion is made of a flexible resilient material.

13. A surgical staple remover according to claim 12, wherein said bowed portion is bowed around a transverse axis with respect to a length of said first and second body members, said bowed portion defining a concave side.

14. A surgical staple remover according to claim 13, wherein one of said first and second members has said bowed portion and is arranged so that said concave side faces another of said first and second members.

15. A surgical staple remover according to claim 13, wherein each of said first and second members have bowed portions arranged so that said concave sides face each other.

16. A surgical staple remover, comprising: p1 a first elongate member having a forward first end terminating in two spaced anvil members and a rearward second end;
   a second elongate member having a forward first end terminating in a blade member adapted to fit between said two spaced anvil members, and a rearward second end;
   means for pivotably linking said first end of said first member and said first end of said second member at a pivot point positioned rearwardly of said blade member and said anvil members; and
   means for joining said second end of said first member and said second end of said second member, at least one of said first and second members being bowed along at least a portion of a length thereof between said first and second end, whereby compression of said first and second members toward each other results in pivot of at least one of said blade member and said anvil members relative to the other of said blade member and said anvil members around said pivot point wherein said means for pivotably linking comprises a notch defined on one of said first and second members and having a rearwardly facing opening, and means located on the other of said first and second members for being pivotably received in said notch, whereby said means for pivotably linking is releasable by rearwardly displacing said other of said first and second members relative to said one of said first and second members so as to remove said means for being pivotably received from said rearwardly facing opening of said notch.

17. A surgical staple remover according to claim 16, wherein said means for pivotably linking comprises means located on at least one of said first and second members for pivotably and releasably receiving the other of said first and second members in a linked position.

18. A surgical staple remover according to claim 17, wherein said joining means comprises means for releasably joining said second ends of said first and second members with said means for pivotably linking in said linked position, wherein release of said joining means allows release of said means for pivotably linking whereby said first and second members are separable from each other.

19. A surgical staple remover according to claim 16, wherein said joining means further comprises means for releasably holding said other of said first and second members against rearward displacement relative to said one of said first and second members.

* * * * *